United States Patent [19]

Hecht et al.

[11] Patent Number: 5,221,537
[45] Date of Patent: Jun. 22, 1993

[54] TISSUE IRRIGATING SOLUTIONS

[76] Inventors: Gerald Hecht, 6201 Wheaton Dr., Fort Worth, Tex. 76133; Michael E. Stern, 2300 Grayson Dr., Apt. 1921, Grapevine, Tex. 76051; Romulus K. Brazzell, 4514 Lake Park, Arlington, Tex. 76016

[21] Appl. No.: 914,650

[22] Filed: Jul. 13, 1992

Related U.S. Application Data

[63] Continuation of Ser. No. 586,364, Sep. 21, 1990, abandoned, which is a continuation of Ser. No. 239,887, Sep. 2, 1988, abandoned.

[51] Int. Cl.$^5$ .................. A61K 33/42; A61K 33/14; A61K 33/00; A61K 37/00; A61K 31/70; A61K 31/205; A61K 31/195; A61K 31/13

[52] U.S. Cl. ......................... 424/601; 424/665; 424/678; 424/679; 424/680; 424/681; 424/717; 514/2; 514/23; 514/554; 514/562; 514/665; 514/912

[58] Field of Search .............. 514/912, 913, 914, 915, 514/563, 564, 562, 665, 2, 23, 554; 424/601, 665, 678, 679, 680, 681, 717

[56] References Cited

U.S. PATENT DOCUMENTS

| | | | |
|---|---|---|---|
| 4,002,758 | 1/1977 | Bigou | 424/263 |
| 4,443,432 | 4/1984 | Gerabedian et al. | 424/127 |
| 4,550,022 | 10/1985 | Garabedian et al. | 424/127 |
| 4,725,586 | 2/1988 | Lindstrom et al. | 514/59 |
| 4,775,531 | 10/1988 | Gilbard | 514/915 |
| 4,794,124 | 12/1988 | Yamamoto et al. | 514/912 |

OTHER PUBLICATIONS

Martindale, The Extra Pharmacopoeia (28th ed. 1982) p. 50.

McEnerney et al., "Simplification of Glutathione Bicarbonate Ringer Solution Its Effect on Corneal Thickness," *Investigative Ophthalmology and Visual Science*, 16(7), Jul., 1977.

Meister, "Selective Modification of Glutathione Metabolism," *Science*, vol. 220, No. 4596, pp. 472-477, Apr., 1983.

O'Malley, "Salt Contamination of the Eye, an Infusion Hazard," *Ocutome/Fragmatome Newsletter*, vol. 4(14), 1979.

J. Worst, *American Intraocular Implant Society Journal*, (Jan., 1978).

Primary Examiner—Frederick E. Waddell
Assistant Examiner—Raymond J. Henley, III
Attorney, Agent, or Firm—Sally S. Yeager

[57] ABSTRACT

Irrigating solutions with thiol or disulfide containing compounds in physiologically acceptable salt solutions are described. The irrigating solutions are useful during surgery, particularly ophthalmic, neural, cardiovascular or otic surgery, to stabilize the affected tissue. Methods for their preparation and use are described.

4 Claims, No Drawings

TISSUE IRRIGATING SOLUTIONS

This application is a continuation of application Ser. No. 07/587,364, filed on Sep. 21, 1990, now abandoned, which is a continuation of Ser. No. 07/239,887 filed on Sep. 2, 1988, now abandoned.

BACKGROUND OF THE INVENTION

1. Field of the Invention

This invention relates to irrigating solutions for use within the human body and more particularly to solutions useful for irrigating tissues during surgery, such as ophthalmic, neural, cardiovascular or otic surgery.

2. Discussion of Related Art

Any scission into the body is detrimental and invariably results in cell loss. The need to keep cell loss to a minimum is particularly crucial during any surgical procedure performed on delicate and irreplaceable tissues, for example, ophthalmic or nerve tissue.

The cornea of the eye is comprised of five layers: epithelium, Bowman's membrane, stroma, Descemet's membrane, and endothelium. The endothelium layer is particularly vulnerable to trauma, and since this layer is only a single cell in depth, protection of the endothelium is particularly important because endothelial cells are infrequently, if ever, replaced as a normal process in adult life. The corneal endothelium is principally responsible for maintaining proper hydration of the stromal layer. The stromal layer has a tendency to imbibe fluid, a tendency which is counterbalanced by outward fluid transport via the endothelium. If the proper fluid balance is not maintained in the stromal layer, the cornea thickens and the characteristic transparency of the cornea is lost. Accordingly, cell loss or damage in the endothelial layer results in decreased vision. Failure of the endothelium to perform its fluid transport function for even short periods of time will result in corneal thickening and visual clouding. Because of the importance and vulnerability of the endothelial layer, it is necessary during eye surgery, such as cataract and retinal surgery or corneal transplants, to make provisions for the protection of the endothelial cells.

A significant factor causing cell loss during tissue scission is the traumatic change in environment experienced by the cells. Exposure to the atmosphere presents a far different environment for internal cells than is provided by the natural fluids in which they are bathed. To simulate the natural cellular environment during surgery thereby preventing cell damage, exposed tissue is frequently irrigated in solutions which attempt to approximate the chemical composition and/or physical properties of natural body fluids. The value of bathing ophthalmic tissue during surgery to prevent cell damage has long been recognized. For internal ocular tissues, such as the endothelium, the aqueous humor is the natural bathing fluid. Therefore, an ideal ophthalmic irrigating solution should simulate or surpass the cell preservation properties of the aqueous humor.

Of primary concern for any tissue irrigating solution is that the osmolality of the solution be generally isotonic relative to cellular fluids, so as to maintain equal osmotic pressure within and without the cell membranes. To this end, one of the early ophthalmic irrigating solutions was isotonic (0.9%) saline. However, it has long been recognized that isotonic saline is quite inadequate as an ophthalmic irrigating solution because its use has been shown to result in endothelial cell swelling, cell damage, and consequent corneal clouding.

Because of the inadequacy of isotonic saline, various alternative electrolyte solutions have been proposed as irrigating solutions, particularly ophthalmic irrigating solutions which more closely resemble the aqueous humor and prevent or reduce cell damage and corneal clouding. Standard electrolyte solutions primarily intended for injection, such as Ringer's solution and lactated Ringer's solution, have been used as ophthalmic irrigating solutions because they are readily available and are sterile.

An electrolyte solution specifically intended for ophthalmic irrigation is available from Alcon Laboratories, Inc. as BSS ®. That solution contains the essential ions calcium, sodium, potassium, magnesium and chloride in generally optimal concentrations for ocular tissue. In addition the solution contains acetate and citrate, natural components of tear fluid.

Electrolyte solutions used for ophthalmic irrigation such as lactated Ringer's solution and balanced salt solutions represent improvements over normal saline because they provide necessary ions in addition to the sodium and chloride ions provided by isotonic saline. For example, magnesium is an important cofactor for adenosine triphosphatase, an enzyme which plays an important role in mediating the fluid transport pump in the eye. Calcium is necessary to maintain the endothelial junction, and potassium is an important factor in many biochemical processes. Moreover, the fluid transport pump of the endothelium requires a proper sodium, potassium ion ratio ($Na^+/K^+$) to function. These additions to previously known electrolyte solutions used to irrigate ocular tissue have reduced, but not eliminated, corneal swelling and cell damage during surgery.

The need for improved ophthalmic irrigating solutions continues, particularly in view of new surgical techniques which may probe deeper into the eye requiring several hours of operating time. For example, surgical advances now permit surgery in the vitreous (posterior) chamber to remove opacified vitreous humor or to repair retinal detachment. Such operations can require up to three hours. The risk of damage to internal cells resulting from exposure during surgery increases the longer the cells are exposed.

During eye surgery and particularly during surgery which requires extended periods of time, proper electrolytic balance alone is insufficient to protect the corneal endothelium. To prevent cell damage and maintain proper corneal thickness, an irrigating solution, in addition to maintaining electrolytic balance, must provide metabolic support and must particularly provide factors needed for the enzyme-mediated sodium/potassium ion pump system through which excess fluid is removed from the stroma.

Factors which have been determined to be necessary for sustained metabolism of endothelial cells include dextrose, glutathione and bicarbonate. All have been shown to be important in maintaining the structural integrity of endothelial cells. Dextrose provides an energy source for the cells by serving as a substrate for various metabolic pathways; and glutathione has been shown to aid the adenosine-triphosphatase mediated metabolic pump by maintaining the proper sodium, potassium ion ratio. In addition, bicarbonate is useful in maintaining proper pH of the irrigating solution.

Glutathione bicarbonate-Ringer's solution (GBR) has incorporated the above-mentioned factors and is effective in maintaining corneal thickness and endothelial cell integrity for up to three hours. However, its use has been limited for reasons of sterility and stability.

Sterility of an ophthalmic irrigating solution is absolutely essential. Although a solution will perfuse the eye in essentially a closed system, even a small number of microorganisms can produce an overwhelming endophthalmitis. Therefore, it is important that irrigating solutions be free of pathogens such as pseudomonas, an organism that has very few metabolic requirements and can grow with a minimal nutrient supply; see J. Worst, *American Intraocular Implant Society Journal* (January, 1978) reporting on a series of infections in Europe due to pseudomonas-contaminated irrigating solutions. Sterility can be ensured through prepackaging so that quality and sterility can be closely monitored and tested.

A significant problem with GBR is that it may not be prepackaged due to the long term incompatibility and/or instability of its various moieties. Of the moieties added to Ringer's solution to formulate GBR, bicarbonate is perhaps the most important, McEnerney et al. *Simplification of Glutathione-Bicarbonate Ringer Solution: Its Effect on Corneal Thickness*, Investigative Ophthalmology and Visual Science, 16, No. 7 (Jul. 1977). Unfortunately the bicarbonate as well as the phosphate in a bicarbonate-phosphate buffer system form insoluble precipitates with magnesium and calcium ions. Although precipitation is not a problem in freshly prepared solutions at the ionic concentrations useful in ophthalmic irrigation, long-term storage is proscribed. As insoluble crystals introduced into the eye will cloud vision, the importance of keeping a tissue irrigating solution free of insoluble precipitates may be readily appreciated. For discussion relating to precipitation of calcium bicarbonate from Ringer's solution containing sodium bicarbonate and dextrose see O'Malley, *Salt Contamination of the Eye—An Infusion Hazard*, Ocutome/Fragmatome Newsletter, 4, No. 14, 1979.

A further factor which proscribes long-term storage of GBR is the unavailability of a proper pH at which all of the moieties are stable. Several moieties of GBR are unstable at the physiological pH of about 7.4. Below a pH of about 8 bicarbonate generally decomposes producing $CO_2$ and resulting both in a loss of bicarbonate and increased pH. On the other hand, glucose is stable at a pH of less than about 6. Glutathione, while biologically effective either in reduced or oxidized form, is preferred in the oxidized form because the reduced form quickly oxidizes in aqueous solutions, preventing proper labeling of the irrigating solution. However, above pH 5 in admixture with all other components, oxidized glutathione (glutathione disulfide) is unstable over extended periods of time and as a result will gradually decrease to an unacceptably low level.

Problems due to the formation of insoluble precipitates and glutathione instability in an irrigating solution were resolved as set forth in two patents, U.S. Pat. No. 4,550,022 and U.S. Pat. No. 4,443,432, issued to Garabedian, et al. on Oct. 29, 1985 and Apr. 17, 1984, respectively. The entire contents of these two patents are hereby incorporated in the present specification by reference. In those patents the problems of precipitates and instability were surmounted by recognizing the causes of the problems and devising a two-part product approach wherein the parts are combined prior to use. Calcium and magnesium ions are present in one sterile solution which is acidic and separate from a basic solution containing phosphate and bicarbonate ions. Glutathione, being more stable at lower pH, is present in the acidic solution. The two solutions are then mixed just prior to use, preferably within 24 hours of surgery.

Although the two-part solutions described in U.S. Pat. Nos. 4,550,022 and 4,443,432 provide a way to store two stable, sterile solutions that upon mixing provide tissue irrigating solutions having short term stability, there is still a need for improved tissue irrigating solutions and for single solution products having long term stability. Single solution products are desirable due to the relative ease of manufacture and use, and elimination of the risks of possible contamination during mixing.

Accordingly, it is an objective to provide improved irrigating solutions having long term stability which provide for protection of ophthalmic and other tissues by providing the necessary electrolyte and metabolic support during surgery.

SUMMARY OF THE INVENTION

The present invention is directed towards pharmaceutical compositions containing thiol and/or disulfide-containing compounds which are useful as surgical irrigating solutions. The invention is based on the discovery that certain thiol and/or disulfide containing compounds can be used in place of glutathione, thereby avoiding stability problems associated with glutathione, to provide superior tissue irrigating solutions. The compositions of the present invention are particularly useful as ophthalmic irrigating solutions which protect the endothelium during ophthalmic surgery thereby preventing corneal thickening.

The irrigating solutions of the present invention comprise the thiol or disulfide-containing compounds in a physiologically compatible salt solution containing bicarbonate ions, calcium ions, magnesium ions, potassium ions, phosphate ions, chloride ions and sodium ions. The solutions also contain an energy source such as dextrose, lactate or lactic acid. The solutions have a pH of between about 6.8 and 8.2 and an osmolality (mOsm/Kg) of between about 260 and 340.

The invention is also directed towards methods of using the solutions during surgery for the protection of tissues. In particular the solutions can be used during ophthalmic, neural, cardiovascular or otic surgery.

DETAILED DESCRIPTION OF THE PREFERRED EMBODIMENTS

Glutathione, found in virtually all cells, is recognized as an important factor in various cellular functions. For example, glutathione is involved in the reduction of disulfide linkages of proteins, the synthesis of deoxyribonucleotide precursors of DNA and the protection of cells against the effects of free radicals and reactive oxygen intermediates formed during metabolism, see Meister, *Selective Modification of Glutathione Metabolism:* Science, Volume 220, No. 4596, pp. 472–477 (Apr.1983). Its presence in the aqueous humor of the eye is necessary for regulation of the proper sodium, potassium ion ratio in the cornea.

Glutathione is a tripeptide consisting of the amino acids cysteine, glutamic acid and glycine. All of these amino acids are present in normal healthy body tissues where glutathione functions. However, cysteine is found in relatively lower concentrations than glutamic acid and glycine. Where cysteine does exist it is found in equilibrium with the amino acid cystine. The reduction of one cystine molecule results in two cysteine molecules. Because the concentrations of cysteine or cystine are lower than the concentrations of glutamic acid and glycine, it is believed that glutathione concentrations are dependent on the availability of cysteine or cystine. It is believed the cystine or cysteine concentrations are the limiting factors with respect to cellular glutathione concentrations.

Without intending to be bound by any theory, it is believed that it is the —S—S portion of cystine in oxidized glutathione or the —SH portion of cysteine in reduced glutathione that is instrumental in providing protection of the corneal endothelium. If cystine (or cysteine) or any disulfide or thiol containing moiety, which can include precursors to cystine or cysteine, is supplied in an irrigating solution to a surgical site, it alone may function to protect the tissue. It is also believed that cystine, cysteine, or any precursor of the two, may, when administered to a surgical site, with the other amino acids which make up glutathione present at the site, form glutathione, which is known to function in the protection and maintenance of tissues, particularly the endothelium.

The solutions of the present invention include a thiol or disulfide containing compound. Disulfide containing compounds which can be used include: cystine, N,N diacetyl-l-cystine, cystamine,γ-l-glutamyl-l-cysteine disulfide and γ-l-glutamyl glutathione disulfide. Thiol containing compounds which can be used include: N, acetyl-l-cysteine, cystathionine, cysteine, γ-l-glutamyl-l-cysteine and γ-l-glutamyl glutathione.

Thiol compounds are present in the irrigating solutions of the present invention at concentrations of 0.2–2.0 millimolar (mM) preferably about 0.42 mM. Disulfide compounds are present at concentrations of 0.1–1.0 mM, preferably about 0.21 mM.

The compositions of the present invention preferably also contain calcium ions, magnesium ions, potassium ions, sodium ions, chloride ions, phosphate ions, bicarbonate ions, and dextrose, lactate or lactic acid. In the preferred single solution compositions of the present invention, the phosphate concentration is adjusted from those found in prior solutions to a point at which efficacy of the solution is maintained and stability, i.e., lack of precipitates, is attained. Efficacy can be maintained and precipitation prevented if the phosphate concentration is between about 0.4 and 1 mM.

The concentrations of the components of the present solutions, in addition to the thiol or disulfide compound concentrations previously discussed, are preferably as follows: calcium ions 0.2 mM–1.3 mM, magnesium ions 0.75 mM–1.3 mM, potassium ions 4.0 mM–7.0 mM, sodium ions 100.0 mM–200.0 mM, chloride ions 100.0 mM–200.0 mM, phosphate ions 0.2 mM–1.0 mM, bicarbonate ions 15.0 mM–40.0 mM, and dextrose 3.0 mM–7.0 mM or l-lactic acid or its disodium salt 5.0 mM–25.0 mM.

The preferred irrigating composition of the present invention is a single solution comprising: cystine, 0.42 mM; calcium ions 1.05 mM; magnesium ions 0.98 mM; potassium ions 5.1 mM; sodium ions 148.2 mM; chloride ions 131.2 mM; phosphate ions 0.59 mM; bicarbonate ions 25.0 mM; and dextrose 5.11 mM or sodium lactate 10.2 mM.

The solutions of the present invention have a pH range that is best suited for use in the irrigation of body tissues, specifically ophthalmic and neural tissues. The pH range best suited for such use is between about 6.8 and about 8.2, preferably 7.0–7.4. In order to maintain the osmotic stability of the cells of the tissues to be irrigated, the osmolality of the solution should be between about 260 and 340 mOsm/Kg, preferably 305 mOsm/Kg.

Studies have been conducted comparing the efficacy of solutions of the present invention with known irrigating solutions such as BSS Plus ®. In vitro corneal perfusions indicated that solutions of the present invention provided comparable protection for the endothelial cells and therefore the corneas. In addition, the solutions of the present invention do not present the precipitation problems of prior solutions and may be chemically more stable than solutions containing glutathione due to the relative stability of the disulfide and thiol containing compounds which are believed to perform the same cellular maintenance functions as glutathione.

Thiol or disulfide containing compounds according to the present invention can also be added to one of the solutions of the two part product disclosed in U.S. Pat. Nos. 4,550,022 and 4,443,432 issued to Garabedian et al. The compounds can also be substituted for glutathione which is present in the acidic solution of the two part product prior to mixing. The thiol or disulfide containing compound may be included in one or the other parts of the two-part product.

Use of the solutions for irrigating tissue during ophthalmic surgery provides for maintenance of proper corneal thickness and clarity. A solution is used by continuously irrigating the affected tissue during the course of the surgical procedure. In addition, the solutions can be used during other types of surgery as irrigating solutions to stabilize irreplaceable tissue. For example, it is well known that destroyed nerve cells, for the most part, are not regenerated. Partially because of its low cost and ready availability, normal saline is the traditional irrigating solution used in neurosurgery. However, the use of saline has several theoretical disadvantages which may be of unrecognized clinical importance. The pH of saline ranges from 5 –7 and is unbuffered causing an acidic environment. In the absence of circulating cerebro/spinal fluid, as is usually the case in open neurosurgical procedures, this acid pH may cause damage to the exposed tissue of the brain and spinal cord. Use of the irrigating solutions of the present invention provides an alternative to circulating cerebro/spinal fluid or use of normal saline which is inadequate for proper protection of exposed tissues. Once prepared the solutions are sterilized and bottled by suitable techniques, such as terminal sterilization or aeseptic filling, preferably terminal sterilization. The following examples further illustrate the compositions of the present invention and their preparation.

EXAMPLE 1

A solution of the following formula was prepared according to the procedure set forth below.

| Ingredient | Grams |
| --- | --- |
| Calcium Chloride, dihydrate | 0.154 |
| Magnesium Chloride, hexahydrate | 0.200 |
| Potassium Chloride | 0.380 |
| Sodium Chloride | 7.140 |
| Sodium phosphate dibasic | 0.084 |
| Dextrose | 0.920 |
| L-Cystine | 0.100 |
| Sodium Bicarbonate | 2.520 |
| Water for Injection | q.s. 1000 ml |
| 1N HCl | Adjust pH to 7.2 |

| Ingredient | Grams |
|---|---|
| -continued | |
| | (3.2 ml) |

Procedure

A vessel and stir bar were calibrated to a volume of 1000 ml and depyrogenated. Approximately 800 ml of water for injection was added. While stirring the calcium chloride dihydrate, magnesium chloride hexahydrate, potassium chloride, sodium chloride, sodium phosphate dibasic, dextrose, cystine, and sodium bicarbonate were added sequentially allowing each to dissolve before addition of the next. The pH was measured and adjusted to 7.2 with 3.2 ml 1N HCl. Water for injection was added to bring the volume to 1000 ml.

EXAMPLE 2

Additional solutions in accordance with the present invention can be prepared from the following ingredients according to the procedure set forth below.

| Ingredient | Amount |
|---|---|
| Calcium Chloride Dihydrate | 0.12–0.18 mg/mL |
| Magnesium Chloride Hexahydrate | 0.16–0.24 mg/mL |
| Potassium Chloride | 0.3–0.5 mg/mL |
| Sodium Chloride | 5.7–8.6 mg/mL |
| Anhydrous Sodium Phosphate Dibasic | 0.067–0.10 mg/mL |
| Dextrose or | 0.74–1.10 mg/mL |
| l-Sodium Lactate | 1.00–1.25 mg/mL |
| Thiol or Disulfide | (0.0–0.1 mg/mL thiol) or (0–0.2 mg/mL disulfide) |
| Sodium Bicarbonate | 1.4–2.8 mg/mL |
| Water for Injection | QS to final volume |
| Hydrochloric Acid and/or Sodium Hydroxide | Adjust pH to 6.8–8.0 |

Procedure

A compounding vessel and stirring bar are calibrated to the required volume and depyrogenated. Approximately 80% of the water for injection is added to the vessel. About 5 ml of 1N HCl per liter of formulation is added to the vessel with stirring. The calcium chloride dihydrate, magnesium chloride hexahydrate, potassium chloride, sodium chloride, anhydrous sodium phosphate dibasic, dextrose or l-sodium lactate and sodium bicarbonate are added sequentially allowing each to dissolve before addition of the next. The sodium bicarbonate is added last to minimize pH drift. The pH is measured and adjusted to 7.2. Water for injection is added to final volume and the pH remeasured. The solution is then sterile filtered through a 0.22 um filtration unit. The filtered product is put in depyrogenated vials, stoppered and sealed.

We claim:

1. A method for protecting corneal endothelial tissue during ophthalmic surgery, which comprises:
   irrigating the corneal endothelial tissue with an irrigating solution comprising:
   a therapeutic amount of a compound containing a thiol or disulfide moiety selected from the group consisting of: cystine; N,acetyl-1-cysteine; N,N diacetyl-1-cystine; cystamine; cystathionine; cysteine;γ-1-glutamyl-1-cysteine; γ-1-glutamyl glutathione; γ-1-glutamyl-1-cysteine disulfide; γ-1-glutamyl glutathione disulfide; and a physiologically compatible salt solution which comprises: bicarbonate ions at a concentration of between 15.0 mM and 40.0 mM, calcium ions at a concentration of between 0.2 mM and 1.3 mM, magnesium ions at a concentration of between 0.75 mM and 1.3 mM, potassium ions at a concentration of between 4.0 mM and 7.0 mM, phosphate ions at a concentration of about 0.2 mM and 1.0 mM, chloride ions at a concentration of between 100.0 mM and 200.0 mM, sodium ions at a concentration of between 100.0 mM and 200.0 mM, and dextrose at a concentration of between 3.0 mM and 7.0 mM or lactic acid at a concentration of between 5.0 mM and 25.0 mM.

2. The method of claim 1 wherein the concentration of the compound with a thiol moiety is between 0.2 and 2.0 mM or the concentration of the compound with a disulfide moiety is between 0.1 and 1.0 mM.

3. The method of claim 1 wherein the compound is cystine.

4. The method of claim 1 wherein the compound is cystine at a concentration of about 0.42 mM and the physiologically compatible salt solution comprises calcium ions at a concentration of about 1.05 mM, magnesium ions at a concentration of about 0.98 mM, potassium ions at a concentration of about 5.1 mM, sodium ions at a concentration of about 148.2 mM, chloride ions at a concentration of about 131.1 mM, phosphate ions at a concentration of about 0.59 mM, bicarbonate ions at a concentration of about 25.0 mM and dextrose at a concentration of about 5.11 mM or sodium lactate at a concentration of about 10.2 mM.

* * * * *